United States Patent [19]

Malin

[11] Patent Number: 4,463,117

[45] Date of Patent: * Jul. 31, 1984

[54] HEAT STABLE, POLYMER-FORMING COMPOSITION

[75] Inventor: Michael J. Malin, Park Ridge, N.J.

[73] Assignee: Technicon Instruments Corporation, Tarrytown, N.Y.

[*] Notice: The portion of the term of this patent subsequent to Mar. 15, 2000 has been disclaimed.

[21] Appl. No.: 369,486

[22] Filed: Apr. 19, 1982

Related U.S. Application Data

[63] Continuation of Ser. No. 113,480, Jan. 21, 1980, Pat. No. 4,376,839.

[51] Int. Cl.$^3$ .............................................. C08K 5/32
[52] U.S. Cl. .................................... 524/260; 156/57;
523/515; 524/303; 524/304; 524/305; 524/340;
524/392; 524/510; 526/90; 526/103; 528/277;
528/280
[58] Field of Search ............... 523/515; 524/260, 303,
524/304, 305, 392, 340, 510; 204/159.19;
526/103; 528/280

[56] References Cited

U.S. PATENT DOCUMENTS

| | | | |
|---|---|---|---|
| 2,616,875 | 1/1952 | Adams et al. | 526/85 |
| 2,919,259 | 12/1959 | Naylor | 524/303 |
| 3,275,715 | 9/1966 | O'Leary | 524/303 |
| 3,445,424 | 5/1969 | Martinovich | 524/304 |
| 3,573,233 | 3/1971 | Krefeld et al. | 523/515 |
| 4,107,144 | 8/1978 | Russell | 525/212 |
| 4,169,113 | 9/1979 | Passalento et al. | 523/515 |
| 4,376,839 | 3/1983 | Malin | 524/303 |

FOREIGN PATENT DOCUMENTS 1211817 11/1970 United Kingdom .

*Primary Examiner*—J. Ziegler
*Attorney, Agent, or Firm*—Morgan, Finnegan, Pine, Foley & Lee

[57] ABSTRACT

A heat-stable, polymer-forming composition of a polymerizable material, a transition metal compound, a polymer chain terminator, and, optionally, a preventive antioxidant is disclosed as well as particular uses of such composition.

12 Claims, No Drawings

HEAT STABLE, POLYMER-FORMING COMPOSITION

CROSS-REFERENCE TO RELATED APPLICATIONS

This application is a continuation of pending application Ser. No. 113,480, filed Jan. 21, 1980 U.S. Pat. No. 4,376,839.

BACKGROUND OF THE INVENTION

This invention relates generally to the stabilization of a polymerizable composition and the use of such composition, inter alia, as a transfer medium for diagnostic purposes.

In U.S. Pat. No. 4,120,262, commonly assigned, there is described an apparatus for transferring biological substances supported on the surface of a substrate to the receiving surface of a backing element, wherein the transfer medium is pressed between the surfaces of the substrate and backing element so as to encapsulate the substance within the transfer medium, and removing the substrate to expose the encapsulated substance which is supported on the backing element.

In one embodiment of this invention, the adhesive compositions disclosed and claimed herein are effective transfer media in the above-identified apparatus.

Generally, this invention relates to heat-stable, polymer-forming compositions, either heat- or light-curable, which are characterized by rapid cure when exposed to light, if photoinitiated, or to heat, if thermally initiated, and by extreme stability under storage conditions. If the described embodiment, curing of the composition does not affect the morphological or stained characteristics of the encapsulated biological specimen and the refractive index of cured composition closely matches the refractive index of the encapsulated biological specimen and glass. Also, the composition is virtually odor free; has low toxicity, has a moderate viscosity before cure, i.e. 100–200 cps/25° C.; adheres to glass and other surfaces after cure; and is stable for at least 6 months at 45° C. Further, the cured films with encapsulated biological specimens can be stored indefinitely.

In sum, the compositions of this invention find many uses and can be applied broadly in the diagnostic area where biological specimens are to be placed in a protected state for extended periods, without affecting their morphological or stained characteristics. In addition, such compositions can be used as polymeric coatings, per se, and also as adhesive layers in laminated structures.

SUMMARY OF THE INVENTION

In accordance with this invention, there is claimed a heat stable, polymer-forming adhesive or coating composition comprising:
(a) a polymerizable material selected from vinyl, acrylate or methacrylate monomers or a unsaturated polymer containing ethylenic carbon-carbon double bonds;
(b) a transition metal compound selected from transition metal salts or chelates; and
(c) a polymer chain terminating antioxidant.

An additional component (d), a preventive antioxidant, can be included to improve stability by regenerating the polymer chain terminator. In addition, the composition may optionally contain other materials such as glass-adhesion promoters, photo-initiators, thermal-initiators, water scavengers and acid catalysts. Further, a suitable solvent can be used in preparing these compositions. A suitable solvent is one that dissolves the component but does not react with them.

DETAILED DESCRIPTION OF THE INVENTION

The novel compositions of this invention find broad application in many diverse areas beside the previously mentioned diagnostic field including: adhesives and coatings for glass, plastic, wood, silicone rubber, natural rubber and metal.

The compositions disclosed herein are comprised of three basic components namely:
(a) a polymerizable material selected from vinyl, acrylate or methacrylate monomers or a unsaturated polymer containing ethylenic carbon-carbon double bonds;
(b) a transition metal compound selected from transition metal salts or chelates; and
(c) a polymer chain terminating antioxidant.

Also, a preventive antioxidant, component (d), can be included.

The inclusion of the transition metal compound, the chain terminating antioxidant and the preventive antioxidant, which serve as stabilizers, provides a composition, when properly stored, with a stability in excess of 6 months at 45° C. In the absence of the transition metal compound, the composition undergoes gelation which is complete within 24 hr. at 25° C. In the absence of the chain terminating and preventive antioxidant, the composition is stable for one month at 45° C. This appears to indicate a catalytic role for the transition metal cation, i.e., the cation is regenerated. The transition metal cation appears to act as a free-radical decomposer during "dark" storage. These stabilizers protect the monomer system against free-radical induced polymerization during "dark" storage, but do not interfere with the rapid curing of the composition during use as a bonding agent.

Without the transition metal compound, the resulting composition would have a severely curtailed useful life, i.e. it would have to be used within 8 hours after formulation. Otherwise, the composition becomes increasingly more viscous and is then polymerized to a soft gel. Preferably, the polymerizable composition should have flow characteristics between 100–500 cps at 25° C. to find widespread application.

The polymerizable material component (a) can be any vinyl monomer which includes vinyl compounds, acrylates and methacrylates, for example, vinyl chloride, styrene and methylmethacrylate. It can also be any polyvinyl compound, for example, butadiene, ethoxylated bisphenol A dimethacrylate, etc. Such polyvinyl compounds are capable of forming crosslinks in the cured matrix which results in enhanced mechanical strength. In addition, the polymerizable material can be any unsaturated polymer containing double bonds free to react with free radicals, for example, unsaturated polyesters. These substances include the copolymers of glycols, such as ethylene or propylene glycol, and unsaturated acid derivatives, such as maleic or fumaric anhydride.

Such unsaturated polyesters can also be copolymerized with a vinyl monomer, e.g. vinyl acetate, styrene, methyl methacrylate, acrylamide, methacrylic acid, butadiene, divinyl benzene or ethoxylated bisphenol A dimethacrylate. These copolymers are within the scope of polymerizable materials disclosed herein.

Component (b) is any soluble transition metal compound in which the anion is inorganic or organic, for example, $FeCl_3$ or $Fe(CH_3CO_2)_3$ respectively. Other illustrative transition metal cations are $Ni^{2+}$, $Cr^{3+}$, $Ru^{3+}$, $Mn^{2+}$, $Co^{2+}$, $Ti^{3+}$, $Eu^{3+}$ and $Pr^{3+}$.

These metal cations can also be employed in their chelated form, for example, as the acetylacetonate chelate, such as chromium acetylacetonate and titanium acetylacetonate.

Component (c) is a polymer chain terminating antioxidant. The function of such component is to reduce peroxy radicals, so as to yield hydroperoxides. Particularly useful are the p-alkoxyphenols having the formula:

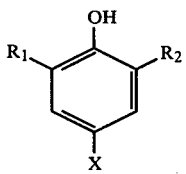

wherein $R_1$ and $R_2$ are each selected from H, phenyl or t-butyl, and X is alkyl or alkyloxy, said alkyl group containing from 1 to 4 carbon atoms. Suitable examples include p-methoxyphenol, 2,6-di-tert-butyl-4-methoxyphenol and 2,6-diphenyl-4-methoxyphenol.

Component (d), optionally included, is a preventive antioxidant which appears to regenerate the chain breaking antioxidant and to decompose hydroperoxides. An example of such preventive antioxidant are β-activated thioethers having the following formula:

$(Y-CH_2CH_2)_2S$ wherein Y can be:

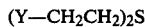

in which Z is H or $NO_2$ or Y can be

where R is an alkyl group containing from 4–18 carbons.

Besides the above three components, other materials can be optionally included as herein discussed to provide useful properties in the composition, both before and after curing.

For example, a glass adhesion promoter can be included, as when a microscope slide is used as the backing material. Suitable glass adhesion promoters include trialkoxysilanes and, preferably, one having a terminal vinyl group such as gamma-(methacryloxy)-propyl-trimethoxysilane. Other employable silanes include those having the formula:

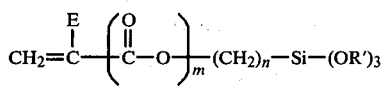

wherein R' is alkyl or alkyloxy, said alkyl containing from 1 to 4 carbons; E is hydrogen or lower alkyl (1–4 carbons); n = 1–10; and m = 0, or 1.

Also, a photo-initiator such as 2,2-dimethoxy-2-phenylacetophenone, 2,2-diethoxyacetophenone or 1-phenyl-1,2-propanedione-2-0-benzoyloxime may be included if curing is to be effected optically.

Alternatively, a thermal initiator, such as benzoyl peroxide, acetylperoxide or azoisobutyronitrile may be included, if curing is to be effected thermally. When cured in this manner, it is preferable to add the initiator just prior to curing. The thermal treatment is effectively achieved by heating at a temperature from about 40° C. to about 200° C.

Optionally, a water scavenger, such as trimethoxyorthoformate or triethylorthoformate may be added to protect the alkoxysilane against attack by water.

To allow efficient operation of the water scavenger, an acid catalyst such as p-toluenesulfonic acid, benzenesulfonic acid or methanesulfonic acid may be added.

It is also within the contemplation of this invention to include an inert solvent for the compositions disclosed herein. A suitable solvent is any solvent which dissolves the components but does not react with them. Suitable solvents include methanol, $CCl_4$ and mixtures of benzene and chloroform. The solvent also serves to control the viscosity of the resulting composition.

The compositions of this invention can effectively be used to bond opaque materials such as wood, metal, plastics and rubber by thermally curing. In the case where the material to be polymerized is exposable to light, photo or radiation curing is the method of choice.

In the preferred embodiment of this invention, the ingredients are used in the following proportionate ranges:

| | |
|---|---|
| (a) polymerizable substance | 80–95% |
| (b) transition metal compound | $1 \times 10^{-4} - 1 \times 10^{-2} M$ |
| (c) chain breaking antioxidant | 0.03–0.3% |
| (d) preventive antioxidant | 0.03–0.3% |

EXAMPLE I

An adhesive composition is prepared by mixing the following ingredients:

| Ingredient | Amount |
|---|---|
| (a) ethoxylated bisphenol A dimethacrylate | 82.0 g. |
| (b) $FeCl_3$ in Methanol $1 \times 10^{-1}$ M solution | 1.0 ml. |
| (c) p-methoxyphenol | 0.3 g. |
| (d) 2,2-dimethoxy-2-phenyl-acetophenone | 2.0 g. |
| (e) trimethylorthoformate | 2.0 g. |
| (f) p-toluenesulfonic acid | 1 mg. |
| (g) gamma-(methacryloxy)-propyltrimethoxysilane | 13.0 g. |

The resulting composition cures rapidly under UV light to provide a useful coverslip for a blood smear or a glass slide.

EXAMPLE II

The composition of Example I is prepared in a solvent medium in which the following solvents or mixtures thereof are employed:
- carbon tetrachloride
- chloroform
- benzene
- methanol The resulting compositions exhibit comparable curing properties and provide equivalent utility.

EXAMPLE III

The composition of Example I is duplicated except that the following thermal initiators, in stoichiometric equivalent amounts, are employed instead of the photoinitiator, component (e). The resulting compositions utilize the solvents indicated:

| benzoyl peroxide | benzene |
|---|---|
| azoisobutyronitrile | methanol |

The thermal initiators are incorporated just prior to thermal treatment which is effected at a temperature of about 100° C. The resulting cured compositions provide effective adhesive compositions.

EXAMPLE IV

The following adhesive composition was prepared with the following ingredients.

| Composition A | |
|---|---|
| Ingredient | Amount |
| (a) ethoxylated bisphenol A dimethacrylate | 82.0 g. |
| (b) FeCl$_3$ in MeOH $1 \times 10^{-1}$ M soln. | 1.0 ml. |
| (c) p-methoxyphenol | 0.3 g. |
| (d) dilaurylthiodipropionate | 0.3 g. |
| (e) 2,2-dimethoxy-2-phenyl-acetophenone | 2.0 g. |
| (f) trimethylorthoformate | 2.0 g. |
| (g) p-toluenesulfonic acid | 1 mg. |
| (h) gamma-(methacryloxy)-propyltrimethoxysilane | 13.0 g. |

In its performance in the aforesaid system, the adhesive composition rapidly cured under UV light to provide a useful coverslip for a blood smear on a glass slide. The cured adhesive film exhibited a refractive index compatible with the encapsulated blood cells and was extremely stable, i.e., storable for an indefinite period of time. The adhesive composition itself had a shelf life of 6 mo/45° C. and virtually no odor or toxicity. It has a viscosity of 100-200 cps/25° C. and adhered very well to glass.

EXAMPLE V

A composition as described in Example IV is prepared except that the following vinyl monomer is used in place of component (a) with comparable results:

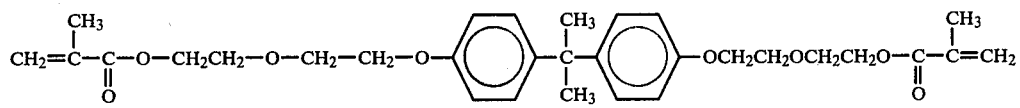

EXAMPLE VI

A composition as described in Example IV is prepared except that the following transition metal compounds are used in place of FeCl$_3$ with comparable results:
- CrCl$_3$
- MnCl$_2$
- FeBr$_3$
- CoCl$_2$
- NiCl$_2$
- RuCl$_3$
- Eu(fod)$_3$; fod = tris(6,6,7,7,8,8-heptafluoro-2,2-dimethyl-3,5-octanedionate)
- chromium acetylacetonate
- titanium acetylacetonate
- ferric acetate
- cobalt oleate
- Pr(fod)$_3$

EXAMPLE VII

A composition as described in Example IV is prepared except that 2,6-di-t-butyl-4-methylphenol is used as the polymer chain terminator to give comparable results.

EXAMPLE VIII

A composition as described in Example IV is prepared except the following preventive antioxidants are used in place of component (d) with comparable results:

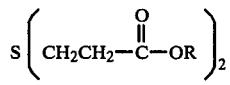

where R = C$_8$H$_{17}$, C$_{18}$H$_{37}$

It should be understood by those skilled in the art that various modifications may be made in the present invention without departing from the spirit and scope thereof as described in the specification and defined in the appended claims.

What is claimed is:

1. A heat-stable, polymer-forming adhesive composition comprising:
   (a) polymerizable material, an unsaturated polymer containing ethylenic carbon-carbon double bonds;
   (b) a transition metal compound derived from a transition element;
   (c) a polymer chain terminating antioxidant; and
   (d) a preventive antioxidant for decomposing hydroperoxide, wherein the resulting composition is a stable, storable, pourable liquid which is curable to a solid polymer on initiation of a curing step.

2. A composition as claimed in claim 1 wherein said unsaturated polymer is an unsaturated polyester derived from the condensation of glycols such as ethylene or propylene glycol with fumaric anhydride or maleic anhydride.

3. A composition as claimed in claim 1 wherein said transition metal compound is selected from chromium, manganese, nickel, iron, or cobalt metal salts.

4. A composition as claimed in claim 3 wherein said transition metal compound is a ferric metal salt.

5. A composition as claimed in claim 4 wherein said ferric metal salt is ferric chloride.

6. A composition as claimed in claim 1 wherein said polymer chain terminating antioxidant is a p-alkoxyphenol of the formula:

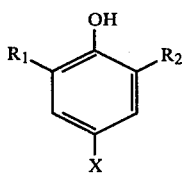

wherein $R_1$ and $R_2$ are each selected from the group consisting of H, phenyl and t-butyl, and X is alkyl or alkyloxy and said alkyl group containing from 1 to 4 carbon atoms.

7. A composition as claimed in claim 6 wherein said p-alkoxyphenol is selected from p-methoxyphenol, 2,6-di-t-butyl-4-methoxyphenol or 2,6-diphenyl-4-methoxyphenol.

8. A composition as claimed in claim 1 wherein said preventive antioxidant is a compound of the formula:

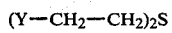

wherein Y is

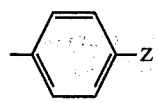

in which Z is selected from the group consisting of H and $NO_2$; or Y is

in which R is alkyl containing from 4–18 carbons.

9. A composition as claimed in claim 8 wherein said preventive antioxidant is dilaurylthiodipropionate.

10. A composition as claimed in claim 1 which is essentially free of an inert solvent.

11. A composition as claimed in claim 1 wherein a photo initiator is included.

12. A composition as claimed in claim 1 wherein a thermal initiator is included.

* * * * *

UNITED STATES PATENT AND TRADEMARK OFFICE
CERTIFICATE OF CORRECTION

PATENT NO. : 4,463,117
DATED : July 31, 1984
INVENTOR(S) : Michael J. Malin

It is certified that error appears in the above-identified patent and that said Letters Patent is hereby corrected as shown below:

Section [57], page 1 of printed patent

After paragraph entitled ABSTRACT, change "12 Claims, No Drawings" to -- 13 Claims, No Drawings --.

Claim (Col. 8, line 30, insert claim 13 as follows:

-- 13. A composition as claimed in claim 1 wherein said resulting composition contains about 1% by weight of inert solvent. --

Signed and Sealed this

Fifth Day of March 1985

[SEAL]

Attest:

DONALD J. QUIGG

Attesting Officer

Acting Commissioner of Patents and Trademarks